(12) United States Patent
Crews

(10) Patent No.: US 7,490,738 B2
(45) Date of Patent: Feb. 17, 2009

(54) MIXING AND DISPENSING FLUID COMPONENTS OF A MULTICOMPONENT COMPOSITION

(75) Inventor: Samuel T. Crews, Palo Alto, CA (US)

(73) Assignee: Angiotech Pharmaceuticals (US), Inc., North Bend, WA (US)

( * ) Notice: Subject to any disclaimer, the term of this patent is extended or adjusted under 35 U.S.C. 154(b) by 274 days.

(21) Appl. No.: 10/957,493

(22) Filed: Oct. 1, 2004

(65) Prior Publication Data

US 2006/0071025 A1    Apr. 6, 2006

(51) Int. Cl.
*B67D 5/60* (2006.01)
(52) U.S. Cl. .................... 222/145.5; 222/1; 222/132; 222/135; 222/145.6; 222/195; 222/394; 239/427.5; 239/428; 604/82; 604/191
(58) Field of Classification Search ............ 222/145.5, 222/135, 145.6, 195, 145.1, 386, 394, 137, 222/132, 1; 239/427.5, 428; 604/82, 191
See application file for complete search history.

(56) References Cited

U.S. PATENT DOCUMENTS

| | | | |
|---|---|---|---|
| 3,117,696 A | 1/1964 | Herman et al. | |
| 3,159,312 A | 12/1964 | Van Sciver | |
| 3,168,967 A | 2/1965 | Giampa | |
| 3,200,995 A | 8/1965 | Gangwisch | |
| 3,236,418 A | 2/1966 | Dalle et al. | |
| 3,884,388 A | 5/1975 | Holcomb | |
| 4,286,734 A | 9/1981 | Tonge | |
| 4,305,672 A | 12/1981 | Adams | |
| 4,359,049 A * | 11/1982 | Redl et al. | 604/82 |
| 4,631,055 A * | 12/1986 | Redl et al. | 604/82 |
| 4,676,657 A | 6/1987 | Botrie | |
| 4,688,702 A | 8/1987 | Yeames | |
| 4,913,553 A | 4/1990 | Falco | |
| 4,923,121 A | 5/1990 | Boyer | |
| 4,995,540 A * | 2/1991 | Colin et al. | 222/132 |
| 5,116,315 A | 5/1992 | Capozzi et al. | |
| 5,200,267 A | 4/1993 | Bauer et al. | |
| 5,219,097 A * | 6/1993 | Huber et al. | 222/145.2 |
| 5,330,424 A | 7/1994 | Palmer et al. | |

(Continued)

FOREIGN PATENT DOCUMENTS

WO    WO-89/05189    6/1989

(Continued)

*Primary Examiner*—Frederick C. Nicolas
(74) *Attorney, Agent, or Firm*—Morrison & Foerster LLP

(57) ABSTRACT

A device for dispensing a multicomponent composition composed of a mixture of different fluid components includes a first and at least a second fluid component inlet. The device also includes a mixing area located downstream from the fluid component inlets and an outlet extending from the mixing area. Each of the fluid component inlets is adapted to communicate with a source of a different fluid component. The mixing area is adapted to receive a flow of a first and at least second fluid component. Within the mixing area, the flow of the first fluid component is disrupted to allow mixing with the flow of a second fluid component to form a flow of multicomponent composition. The mixing area is further adapted to disrupt the flow of the multicomponent composition before the flow of the multicomponent composition exits through the outlet.

19 Claims, 4 Drawing Sheets

U.S. PATENT DOCUMENTS

| | | |
|---|---|---|
| 5,673,857 A | 10/1997 | Meroni et al. |
| 5,676,280 A | 10/1997 | Robinson |
| 5,722,950 A | 3/1998 | Fujita et al. |
| 5,887,755 A * | 3/1999 | Hood, III .................... 222/135 |
| 5,989,215 A | 11/1999 | Delmotte et al. |
| 6,132,396 A | 10/2000 | Antanavich et al. |
| 6,165,201 A | 12/2000 | Sawhney et al. |
| 6,206,905 B1 * | 3/2001 | Holm et al. ................. 606/214 |
| 6,264,113 B1 | 7/2001 | Dingler |
| 6,723,067 B2 * | 4/2004 | Nielson ....................... 604/82 |
| 6,851,627 B2 | 2/2005 | Hashish et al. |
| 2002/0138038 A1 | 9/2002 | Ljungquist |
| 2004/0104244 A1 | 6/2004 | Cline et al. |
| 2005/0087623 A1 | 4/2005 | Finn |
| 2005/0119424 A1 | 6/2005 | Ishii et al. |

FOREIGN PATENT DOCUMENTS

| | | |
|---|---|---|
| WO | WO-94/03218 | 2/1994 |
| WO | WO-2005/046852 | 5/2005 |

\* cited by examiner

MIXING AND DISPENSING FLUID COMPONENTS OF A MULTICOMPONENT COMPOSITION

BACKGROUND

1. Technical Field

The present application generally relates to dispensing a multicomponent composition comprised of a mixture of different fluid components. More particularly, this application relates to dispensing a multicomponent composition using a mixing area to disrupt the flow of one or more fluid components within the mixing area to mix and dispense the mixture through an outlet.

2. Description of Related Art

Surgical adhesives are used in addition or as an alternative to fasteners such as sutures or staples, to join tissue surfaces. For example, biologically and non-biologically based surgical adhesives may be formed by mixing two reactive fluid components. Once the components react with each other, a network may be formed. Depending on the chemistry of the particular adhesive, reaction time may occur quickly, e.g., on the order of seconds. Quick reactions limit the time available for application of the adhesive to a target tissue site. In addition, partial mixing may result in the formation of weak spots. Thus, it is desirable to minimize the amount of time required to mix the fluid components together thoroughly prior to delivery to the target site.

Similarly, various biocompatible materials can be used as tissue sealants, hemostatic agents or for adhesive prevention and for barrier formation. Tissue sealants can be used to seal tissue surfaces, suture lines, and synthetic grafts. For example, mixtures of polyethylene glycols (PEG) can be combined to form a surgical sealant to stop leaks in blood vessels. When combined, the PEGs form a glue-like product in seconds which seals an area to which it is applied. Thus, such agents can be used to seal leaks around sutures, staples in blood vessels. Because formation of the glue-like substance which forms the seal occurs in a matter of seconds, it is essential to rapidly and thoroughly mix the fluid components and dispense the resulting mixture before solidification has occurred.

Numerous technologies are known for mixing and dispensing multicomponent compositions. For example, in the context of surgical adhesives, a first fluid component of a surgical adhesive may be applied directly onto a target site, followed by the application of a second fluid component onto the first fluid component layer. Once dispensed, the two fluid components may be mixed using a surgical instrument and spread over the target area. Alternatively, the two fluid components may be premixed and applied to the target site.

In addition, devices that bring fluid components together for mixing and that apply the mixed adhesive in either an aerosol or a stream form to a target site are known. In some instances, a device may separately atomize the fluids outside the device for contact, mixing, and deposition on the target site. Alternatively, fluid components may be mixed within a device.

Conventional devices that mix fluid components, however, tend to provide inadequate mixing. This is a problem especially in cases where reactive fluid components that solidify shortly after mixing and dispensing are prepared. In such instances, internal mixing devices must be capable of thorough and rapid mixing in order to allow dispensing of homogenous mixtures before solidification occurs. Conventional devices provide inadequate mixing of reactive components which can lead to non-uniformity in the consistency of material delivered, with some areas receiving an over or under solidified preparation.

SUMMARY

In one exemplary embodiment, a device mixes and dispenses a multicomponent composition comprising a mixture of different fluid components. The devices include a first and at least a second fluid component inlet, a mixing area located downstream from the fluid component inlets, and an outlet extending from the mixing area. Each of the fluid component inlets is adapted to communicate with a source of a different fluid component. The mixing area is adapted to receive a flow of a first and at least a second fluid component. Within the mixing area, the flow of the first fluid component is disrupted to allow mixing with the flow of the second fluid component to form a flow of multicomponent composition. The mixing area is further adapted to disrupt the flow of the multicomponent composition before the flow of the multicomponent composition exits through the outlet.

DETAILED DESCRIPTION

Figure 1A:
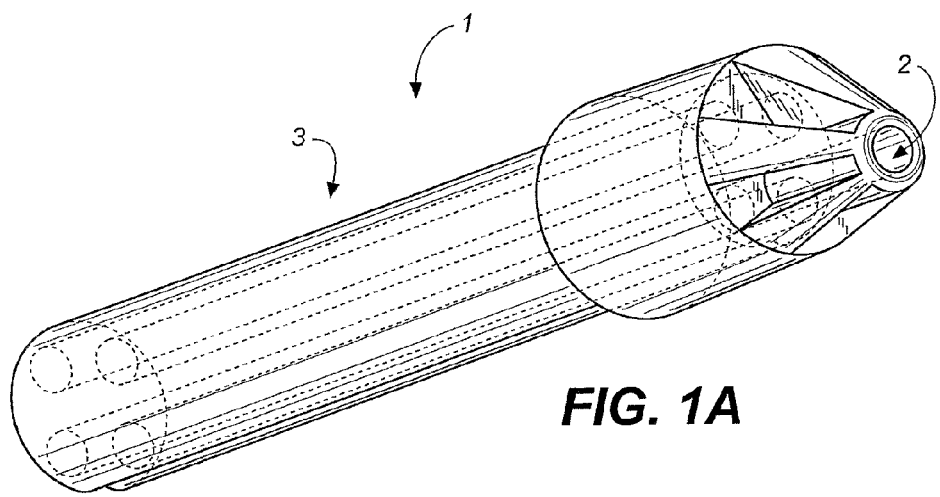
FIGS. 1A and 1B are perspective views of an exemplary embodiment.
Figure 1B:
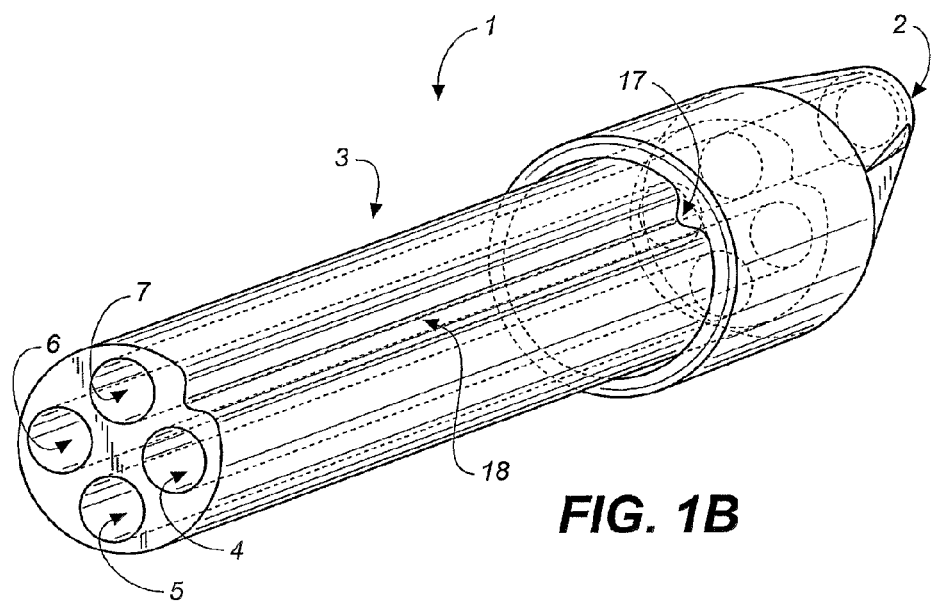

FIGS. 1A and 1B illustrate an exemplary embodiment of a device 1 to mix and dispense multicomponent compositions comprised of a plurality of different fluid components. In the present exemplary embodiment, device 1 includes a plurality of fluid component inlets 4, 5, 6, and 7. Although four fluid component inlets are depicted, it should be recognized that device 1 can include any number of fluid component inlets. Fluid component inlets 4, 5, 6, and 7 communicate with a mixing area 8. Connected to the mixing area 8 is an outlet 2 from which mixed fluid components are expelled.

As exemplified in FIGS. 1A and 1B, fluid component inlets 4, 5, 6, and 7 can be formed as lumens within a tube member 3. As depicted in FIGS. 1A and 1B, the lumens corresponding to fluid component inlets 4, 5, 6, and 7 can traverse the length of tube member 3. In an exemplary embodiment, the lumens are in fluid contact with different sources of fluid components and optionally at least one of these lumens is in communication with a source of pressurized carrier gas to form a carrier fluid inlet.

Figure 2A:
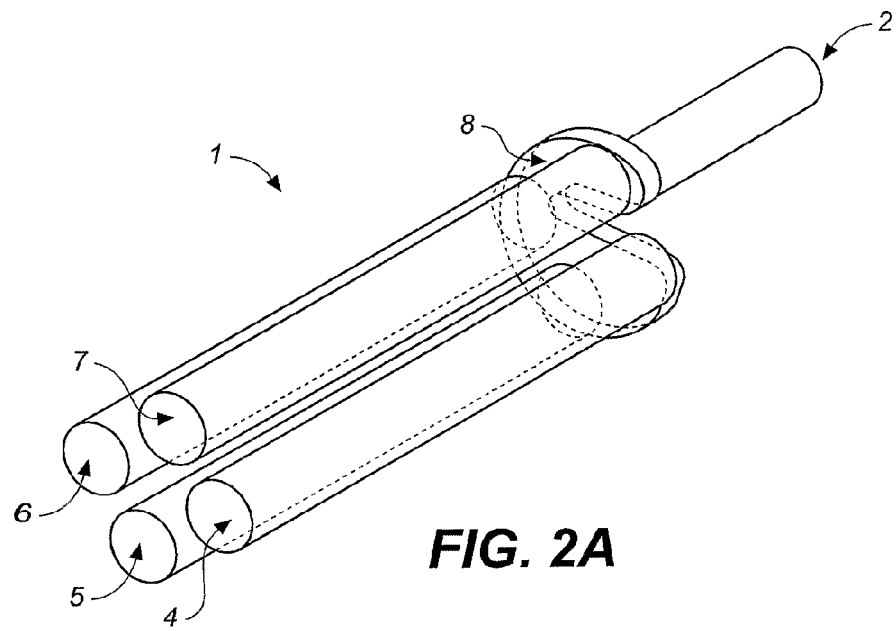
FIGS. 2A and 2B are perspective views of a portion of the exemplary embodiment depicted in FIGS. 1A and 1B.
Figure 2B:
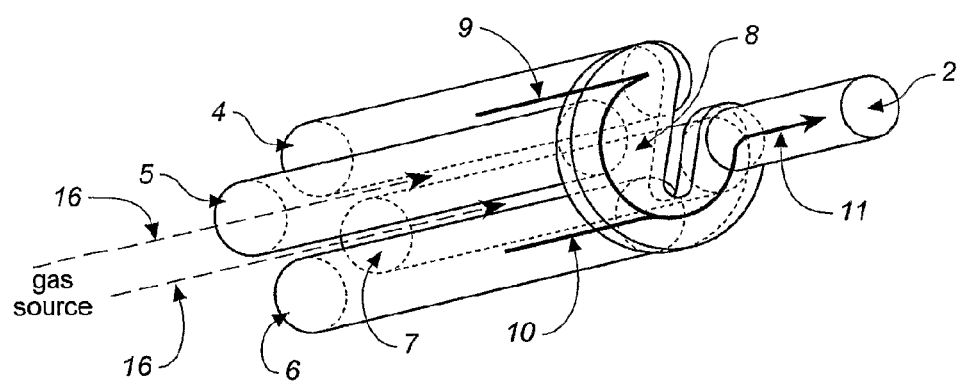
Figure 3A:
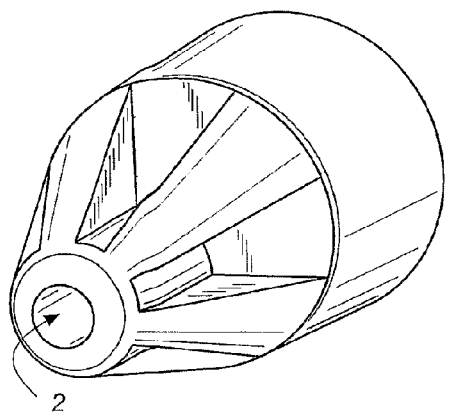
FIG. 3A is a perspective view of a portion of the exemplary embodiment depicted in FIGS. 1A and 1B.
Figure 3B:
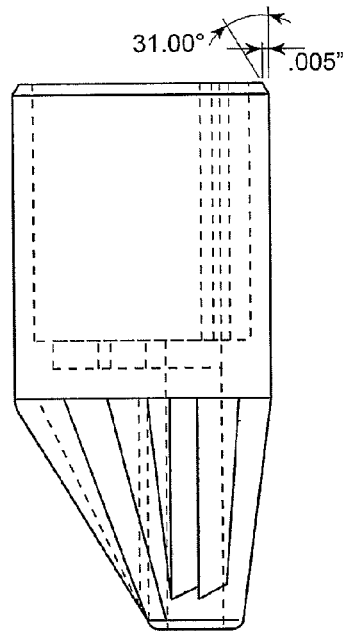
FIG. 3B is a top view of a portion of the exemplary embodiment depicted in FIGS. 1A and 1B.
Figure 3C:
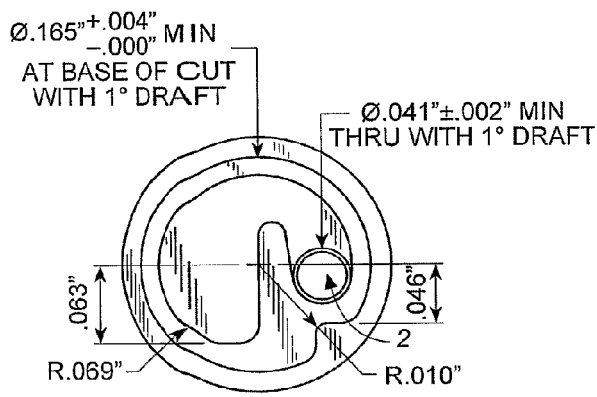
FIG. 3C is a back view of a portion of the exemplary embodiment depicted in FIGS. 1A and 1B.
Figure 3E:
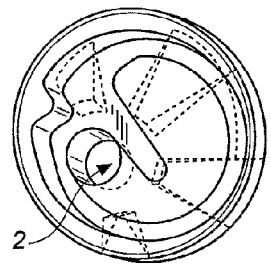
FIG. 3E is a front view of a portion of the exemplary embodiment depicted in FIGS. 1A and 1B.
Figure 3D:
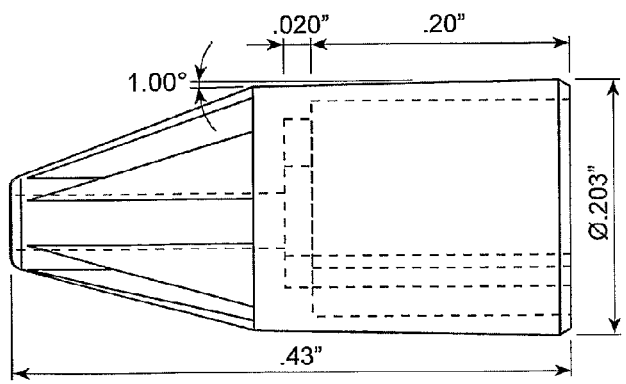
FIG. 3D is a side view of a portion of the exemplary embodiment depicted in FIGS. 1A and 1B.

For example, in the exemplary embodiment depicted in FIGS. 1A and 1B, fluid component inlets 4 and 6 can each provide fluid communication with a different source of a fluid component. Fluid component inlets 5 and 7 can each provide fluid communication with a source of pressurized carrier gas. In FIG. 2B, dotted line 16 shows the flow path of pressurized carrier gas through fluid component inlets 5 and 7. As further shown in FIGS. 2A and 2B, the lumen corresponding to fluid component inlet 7 is aligned with outlet 2. In some embodiments, fluid component inlets 5 and 7 for a carrier fluid can be in communication with a single source of carrier fluid, such as an inert gas via a splitter or manifold, although a plurality of carrier fluid sources may be advantageously used as well in certain instances.

In general, any of a number of carrier fluids may be used. For example, the carrier fluid may be gaseous and/or liquid in nature. Typically, however, the carrier fluid is chemically inert with respect to the fluid components. Suitable inert gases include, without limitation, air, carbon dioxide, nitrogen, argon, helium, gaseous perfluorinated alkanes and ethers, gaseous chlorofluorocarbons, and the like. Suitable inert liquids include, without limitation, polysiloxanes, perfluroinated polyethers, and the like. Pressurized air represents an economical and practical carrier fluid. Equipment associated with pressurized air is well known in the art and may include pressurized tanks or cylinders as well as compressors.

Any of a number of mechanisms can be used to provide motive force to introduce fluid components through the inlets and toward outlet 2, such as pumps, compressors, pistons, and the like. In some instances, one or more check valves, e.g., one-way valves, may be provided to prevent any back flow of fluid components. Such check valves may be positioned upstream from mixing area 8, e.g., within the lumens. Such check valves are particularly useful when the lumens are short, e.g., about 2 to about 5 centimeters in length, because the potential for back flow tends to be inversely proportional to the length of the lumens. However, check valves may be employed with longer lumens as well.

Additionally, in some instances, different fluid components can be directed at substantially the same flow rate toward mixing area 8. Alternatively, the fluid components can be directed at different flow rates toward mixing area 8. Typically, when a carrier fluid such as a gas is used, the flow rate of the carrier fluid is higher than that of the fluid components.

In the present exemplary embodiment, mixing area 8 is adapted to receive a flow of a first fluid component from fluid component inlet 4 and a flow of at least a second fluid component from fluid component inlet 6. As depicted in FIG. 2B, mixing area 8 is adapted to cause disruption in the flow of the first fluid component to mix with the flow of the second fluid component to form a multicomponent composition within mixing area 8. Mixing area 8 is also adapted to disrupt the flow of the multicomponent composition before the flow of the multicomponent composition exits through outlet 2. It should be noted that in the present exemplary embodiment, the disruption of fluid flow may refer not only to changes in flow direction, but can also refer to other flow changes, such as increased turbulence in the flows of the first or second fluid components or of the multicomponent composition during transit through mixing area 8.

In the exemplary embodiment depicted in FIG. 2B, mixing area 8 includes an open side where the first and second lumens corresponding to the first and second fluid component inlets 4, 6 terminate. A first surface opposite the end of the first lumen is adapted to disrupt the flow of the first fluid component from fluid component inlet 4. In the exemplary embodiment depicted in FIG. 2B, the first surface is depicted as a wall of mixing area 8. It should be recognized, however, that the first surface can be a separate structure within mixing area 8, such as a tab.

A channel having a first segment 13 then directs the flow of the first fluid to converge with the flow of the second fluid entering mixing area 8 through the second lumen corresponding to fluid component inlet 6. In one exemplary embodiment, a second surface opposite the end of the second lumen is adapted to disrupt the flow of the second fluid component from fluid component inlet 6. In the exemplary embodiment depicted in FIG. 2B, the second surface is depicted as a wall of mixing area 8. It should be recognized, however, that the second surface can be a separate structure within mixing area 8, such as a tab.

Figure 4A:
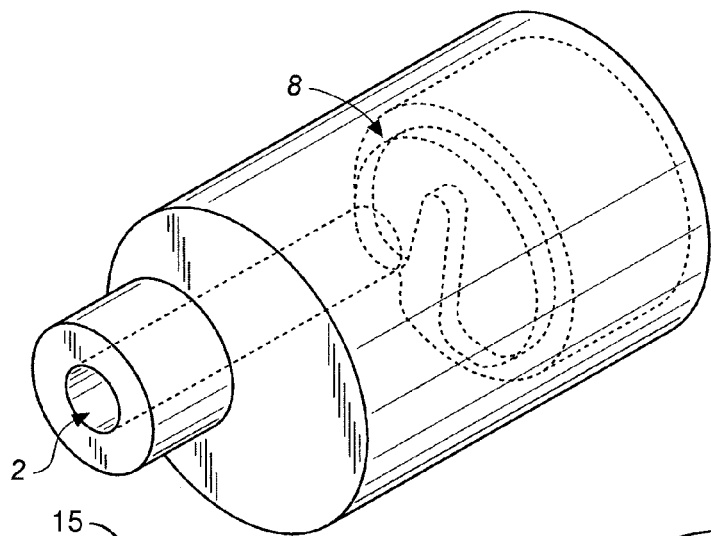
FIG. 4A is a perspective view of a portion of an exemplary embodiment depicted in FIGS. 1A and 1B.
Figure 4B:
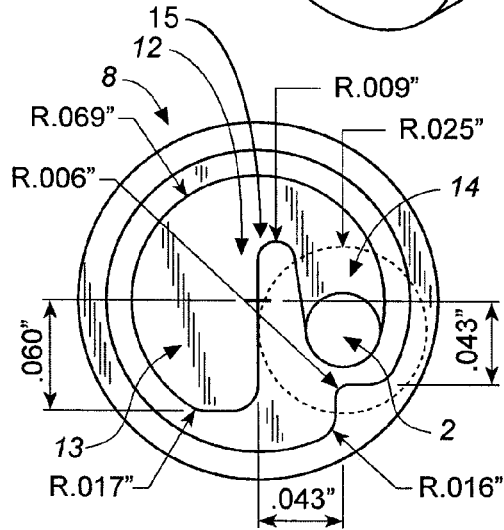
FIG. 4B is a back view of a portion of an exemplary embodiment depicted in FIGS. 1A and 1B.
Figure 4C:
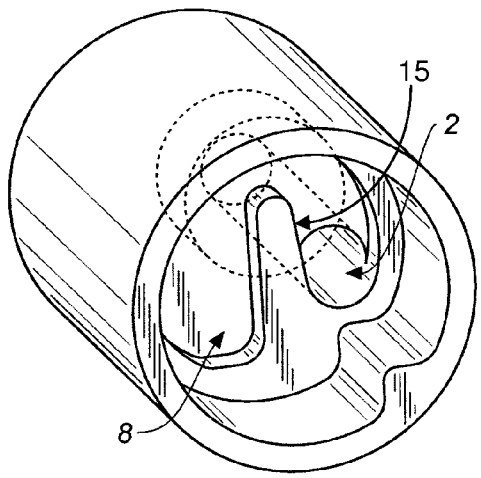
FIG. 4C is another perspective view of a portion of an exemplary embodiment depicted in FIGS. 1A and 1B.
Figure 4D:
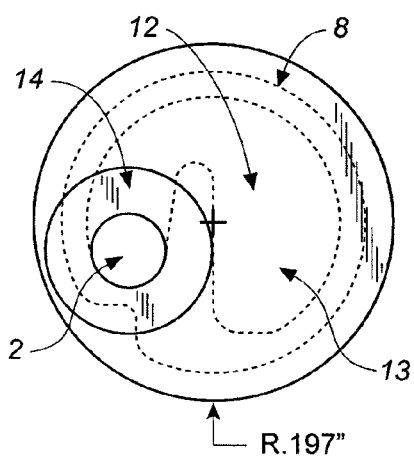
FIG. 4D is a front view of a portion of an exemplary embodiment depicted in FIGS. 1A and 1B.
Figure 4E:
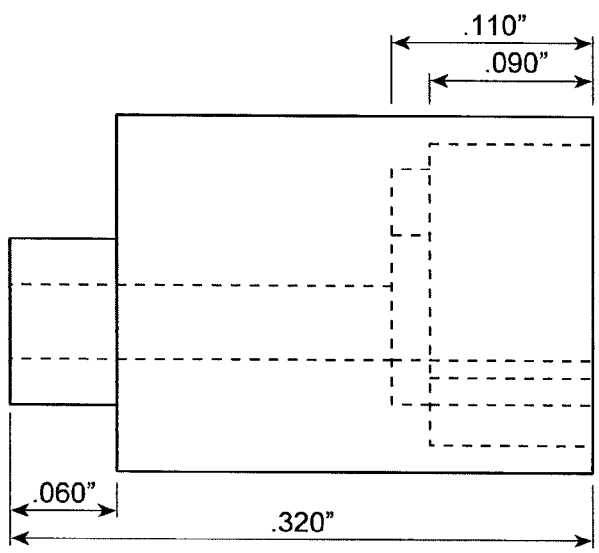
FIG. 4E is a side view of a portion of an exemplary embodiment depicted in FIGS. 1A and 1B.

The first and second fluid components mix to form the multicomponent composition. The channel formed within mixing area 8 is adapted with a second segment 14, which directs the flow of the multicomponent composition to outlet 2. As depicted in FIG. 2B, outlet 2 is formed on the second side of mixing area 8 and is off axis from the lumens corresponding to the first and second fluid component inlets 4, 6. In the exemplary embodiment shown in FIGS. 4B and 4C, mixing area 8 includes a cavity 12 having a protrusion 15 that extends into cavity 12 to define first and second segments 13 and 14 within mixing area 8.

As shown in FIG. 2B, solid lines 9 and 10 indicate the flow paths of the fluid components emerging from fluid component inlets 4 and 6, respectively. Solid line 11 indicates the flow path of the resulting multicomponent composition that results from mixing of the flows from fluid component inlets 4 and 6. In the exemplary embodiment depicted in FIG. 2B, mixing area 8 is adapted to cause the flow of the first fluid component to take a 90 degree turn after the disruption of forward flow by encountering the surface within the mixing area 8, followed by 180 and 90 degree changes in direction of the flow of resulting multicomponent composition. It should be recognized, however, that other angles can be used. Thus, it is expected that variations in mixing area configurations may be developed through routine experimentation.

As shown in FIGS. 3A-E and 4A-D, in one exemplary embodiment, the mixing area 8 can be contained within a nozzle. FIGS. 3A-E show various views of a nozzle that can contain the mixing area of the exemplary embodiment with the dimensions of various features as indicated. FIG. 4A-D shows various views of a portion of the nozzle that can contain the mixing area of the exemplary embodiment with the dimensions of various features as indicated. One of skill in the art will appreciate that these dimensions are not fixed but rather can be changed depending on the requirements of particular applications.

As shown in FIG. 1B, in one exemplary embodiment, the nozzle can have a notch 17 that fits into a groove 18 that runs along at least a portion of the length of the tube member 3 to orient the nozzle to the tube member 3.

In one exemplary embodiment, the portions of the device that contact multicomponent composition and the fluid components thereof should be inert and preferably repellant to the materials contacted. Thus, portions of the device that contact the fluids in operation should be selected according to the fluids themselves. For example, the device or components thereof may be made from a plastic such as polycarbonates, polyurethane, polyesters, acrylics, ABS polymers, polysulfone, and the like. Adhesion inhibiting coatings such as polysiloxanes, perfluorinated polymers, and the like may be used as well. Thus, the mixing area is typically inert and optionally repelling to the fluid components. Similar, lumen surfaces that may contact the fluid components or the carrier fluid are typically inert and optionally repelling to the corresponding fluid as well.

For laparoscopic procedures, the multicomponent composition is typically polymeric in nature, and certain classes of compounds may be particularly preferred to form the polymer composition. For example, synthetic polymers such as poly(acrylic acid), poly(vinyl alcohol), poly(acrylamide), poly(N-isopropylacrylamide), poly(methacrylate), poly(hydroxyethylmethacrylate), poly(vinyl acetate), copolymers and derivatives of these materials may be formed using the invention. However, biocompatible synthetic polymers are preferred for laparoscopic procedures. In addition or in the alternative, naturally occurring compounds such as proteins and saccharides may be used as well. It is well known in the art that such compounds may be used to form sealants that serve as biocompatible adhesive and/or adhesion inhibitors.

Polyethylene glycol (PEG) containing compounds are well known for their biocompatibility. Various forms of PEG are extensively used in the modification of biologically active molecules because PEG can be formulated to have a wide range of solubilities and because it is low in toxicity, antigenicity, immunogenicity, and does not typically interfere with the enzymatic activities and/or conformations of peptides. Further, PEG monomers are generally non-biodegradable and are easily excreted from most living organisms, including humans.

Suitable PEGs include mono-, di-, and multifunctional PEG. Monofunctional PEG has only one reactive hydroxy group, while difunctional PEG has reactive groups at each end. Monofunctional PEG preferably has an average molecular weight between about 100 and about 15,000 daltons, more preferably between about 200 and about 8,000, and most preferably about 4,000. Difunctional and multifunctional PEG preferably have a molecular weight of about 400 to about 100,000, more preferably about 3,000 to about 20,000.

Those of ordinary skill in the art will appreciate that synthetic polymers such as PEG are not currently prepared practically to have exact molecular weights, and that the term "molecular weight" as used herein refers to an average molecular weight of a number of molecules in any given sample, as commonly used in the art. Thus, a sample of PEG 2,000 might contain a statistical mixture of polymer molecules ranging in weight from, for example, 1,500 to 2,500 daltons, with one molecule differing slightly from the next over a range. Specification of a range of molecular weight indicates that the average molecular weight may be any value between the limits specified, and may include molecules outside those limits. Thus, a molecular weight range of about 800 to about 20,000 indicates an average molecular weight of at least about 800, ranging up to about 20 kDa.

PEG can be rendered monofunctional by forming an alkylene ether at one end. The alkylene ether may be any suitable alkoxy radical having 1-6 carbon atoms, for example, methoxy, ethoxy, propoxy, 2-propoxy, butoxy, hexyloxy, and the like. Methoxy is presently preferred. Difunctional PEG is provided by allowing a reactive hydroxy group to exist at each end of the linear molecule. The reactive groups are preferably at the ends of the polymer, but may be provided along the length thereof. Polyfunctional molecules are capable of crosslinking the compositions of the invention, and may be used to attach additional moieties.

In some instances, naturally occurring compounds may be employed. Suitable naturally occurring compounds include, but are not limited to: polysaccharides such as hyaluronic acid, cyclodextrin, hydroxymethylcellulose, cellulose ether, and starch; glycans such glycosaminoglycan and proteoglycan; and various proteins. Proteins such as collagen and other collagenic materials are particularly suited for use.

The device may be advantageously used to form compositions containing collagen as well. It is known in the art that collagen is the major protein component of bone, cartilage, skin, and connective tissue in animals. Collagen, in its native form, is typically a rigid, rod-shaped molecule approximately 300 nm long and 1.5 nm in diameter. It is composed of three collagen polypeptides, which together form a tight triple helix. The collagen polypeptides are each characterized by a long midsection having the repeating sequence -Gly-X-Y-, where X and Y are often proline or hydroxyproline, bounded at each end by the "telopeptide" regions, which constitute less than about 5% of the molecule. The telopeptide regions of the collagen chains are typically responsible for the crosslinking between chains, and for the immunogenicity of the protein. Collagen occurs in several types, having distinct physical properties. The most abundant types are Types I, II and III. Further, collagen is typically isolated from natural sources, such as bovine hide, cartilage, or bones. Bones are usually dried, defatted, crushed, and demineralized to extract collagen, while hide and cartilage are usually minced and digested with proteolytic enzymes (other than collagenase). As collagen is resistant to most proteolytic enzymes, this procedure conveniently serves to remove most of the contaminating protein found with collagen.

Suitable collagenic materials include all types of pharmaceutically useful collagen, preferably types I, II, and III. Collagens may be soluble (for example, commercially available Vitrogen® 100 collagen-in-solution), and may or may not have the telopeptide regions. Preferably, the collagen will be reconstituted fibrillar atelopeptide collagen, for example Zyderm® collagen implant (ZCI) or atelopeptide collagen in solution (CIS). Optionally, colony stimulating factors (CSFs) may be included as well. Various forms of collagen are available commercially, or may be prepared by the processes described in, for example, U.S. Pat. Nos. 3,949,073, 4,488,911, 4,424,208, 4,582,640, 4,642,117, 4,557,764, and 4,689,399. In addition, other forms of collagen are also useful in the practice of the invention, and are not excluded from consideration here. For example, non-fibrillar collagens such as methylated or succinylated collagens may be employed in the present invention. In some instances, collagen crosslinked using heat, radiation, or chemical agents such as glutaraldehyde may be employed. Similarly, gelatin, i.e., collagen denatured typically through boiling, may be suitable.

In some instances, conjugates of the aforementioned materials may be formed. For example, collagenic material may be chemically bound to another polymer, e.g., a synthetic hydrophilic polymer, to form a conjugate. Such collagen-containing conjugates are known in the art and are described, for example, in U.S. Pat. Nos. 5,264,214, 5,304,595, 5,306,500, 5,376,375, 5,413,791, 5,523,348, 5,446,091, 5,543,441, 5,550,188, 5,162,430, 5,328,955, 5,324,775, 5,308,889, 5,292,802, 5,510,418, 5,565,519, 5,470,911, 5,476,666.

The chemical binding can be carried out in a variety of ways. In accordance with one method, the synthetic hydrophilic polymer is activated and then reacted with the collagen. Alternatively, the hydroxyl or amino groups present on the collagen can be activated, and the activated groups reacted with the polymer to form the conjugate. In accordance with another method, a linking group with activated hydroxyl or amino groups therein can be combined with the polymer and collagen in a manner so that it will concurrently react with both the polymer and collagen, forming the conjugate. Since the sealants described herein may be used in the human body, it is important that all of the components of the conjugate, e.g., polymer, collagen, and linking group, singly and in combination, are unlikely to be rejected by the body. Accordingly, toxic and/or immunoreactive components are not preferred as starting materials.

For example, the first step in forming the collagen-polymer conjugates often involves the functionalization of the polymer molecule. Various functionalized PEGs have been used effectively in fields such as protein modification (see Abuchowski et al., Enzymes as Drugs, John Wiley & Sons: New York, N.Y. (1981) pp. 367-383; and Dreborg et al., Crit. Rev. Therap. Drug Carrier Syst. (1990) 6:315, both of which are incorporated herein by reference), peptide chemistry (see Mutter et al., The Peptides, Academic: New York, N.Y. 2:285-332; and Zalipsky et al., Int. J. Peptide Protein Res. (1987) 30:740, both of which are incorporated herein by reference), and the synthesis of polymeric drugs (see Zalipsky et al., Eur. Polym. J. (1983) 19:1177; and Ouchi et al., J. Macromol. Sci. -Chem. (1987) A24:1011. Various types of conjugates formed by the binding of PEG with specific, pharmaceutically active proteins have been disclosed and found to have useful medical applications, in part due to the stability of such conjugates with respect to proteolytic digestion, reduced immunogenicity, and longer half-lives within living organisms.

One form of PEG that has been found to be particularly useful is monomethoxypolyethylene glycol (mPEG), which can be activated by the addition of a compound such as cyanuric chloride, then coupled to a protein (see Abuchowski et al., J. Biol. Chem. (1977) 252:3578, which is incorporated herein by reference). Although such methods of activating PEG can be used in connection with the present embodiment, they are not particularly desirable in that the cyanuric chloride is relatively toxic and must be completely removed from any resulting product in order to provide a pharmaceutically acceptable composition.

Activated forms of PEG can be made from reactants that can be purchased commercially. One form of activated PEG, which has been found to be particularly useful, is mPEG-succinate-N-hydroxysuccinimide ester (SS-PEG) (see Abuchowski et al., Cancer Biochem. Biphys. (1984) 7:175, which is incorporated herein by reference). Activated forms of PEG such as SS-PEG react with the proteins under relatively mild conditions and produce conjugates without destroying the specific biological activity and specificity of the protein attached to the PEG. However, when such activated PEGs are reacted with proteins, they react and form linkages by means of ester bonds. Although ester linkages can be used, they are not particularly preferred in that they undergo hydrolysis when subjected to physiological conditions over extended periods of time (see Dreborg et al., Crit. Rev. Therap. Drug Carrier Syst. (1990) 6:315; and Ulbrich et al., J. Makromol. Chem. (1986) 187:1131, both of which are incorporated herein by reference).

It is possible to link PEG to proteins via urethane linkages, thereby providing a more stable attachment that is more resistant to hydrolytic digestion than the ester linkages (see Zalipsky et al., Polymeric Drug and Drug Delivery Systems, Chapter 10, "Succinimidyl Carbonates of Polyethylene Glycol" (1991) incorporated herein by reference to disclose the chemistry involved in linking various forms of PEG to specific biologically active proteins). The stability of urethane linkages has been demonstrated under physiological conditions (see Veronese et al., Appl. Biochem. Biotechnol. (1985) 11:141; and Larwood et al., J. Labelled Compounds Radiopharm. (1984) 21:603, both of which are incorporated herein by reference). Another means of attaching the PEG to a protein can be by means of a carbamate linkage (see Beauchamp et al., Anal. Biochem. (1983) 131:25; and Berger et al., Blood (1988) 71:1641, both of which are incorporated herein by reference). The carbamate linkage is created by the use of carbonyldiimidazole-activated PEG. Although such linkages have advantages, the reactions are relatively slow and may take 2 to 3 days to complete.

The conjugates formed using the functionalized forms of PEG vary depending on the functionalized form of PEG that is used in the reaction. Furthermore, the final product can be modified with respect to its characteristics by changing the molecular weight of the PEG. In general, the stability of the conjugate is improved by eliminating any ester linkages between the PEG and the collagen, and including ether and/or urethane linkages. However, to promote resorption, weaker ester linkages may be included so that the linkages are gradually broken by hydrolysis under physiological conditions. That is, by varying the chemical structure of the linkage, the rate of resorption can be varied.

Polyfunctional polymers may also be used to crosslink collagen molecules to other proteins (e.g., glycosaminoglycans, chondroitin sulfates, fibronectin, and the like), particularly growth factors, for compositions particularly suited for use in wound healing, osteogenesis, and immune modulation. Such tethering of cytokines to collagen molecules provides an effective slow-release drug delivery system.

Collagen contains a number of available amino and hydroxy groups that may be used to bind the synthetic hydrophilic polymer. The polymer may be bound using a "linking group", as the native hydroxy or amino groups that are present in collagen and in the polymer frequently require activation before they can be linked. For example, one may employ compounds such as dicarboxylic anhydrides (e.g., glutaric or succinic anhydride) to form a polymer derivative (e.g., succinate), which may then be activated by esterification with a convenient leaving group, for example, N-hydroxysuccinimide, N,N'-disuccinimidyl oxalate, N,N'-disuccinimidyl carbonate, and the like. See also Davis, U.S. Pat. No. 4,179,337, for additional linking groups. Presently preferred dicarboxylic anhydrides that are used to form polymer-glutarate compositions include glutaric anhydride, adipic anhydride, 1,8-naphthalene dicarboxylic anhydride, and 1,4,5,8-naphthalenetetracarboxylic dianhydride. The polymer thus activated is then allowed to react with the collagen, forming a collagen-polymer composition used to make the tubes.

For example, a pharmaceutically pure form of monomethylpolyethylene glycol (mPEG) (MW 5,000) may be reacted with glutaric anhydride (pure form) to create mPEG glutarate. The glutarate derivative is then reacted with N-hydroxysuccinimide to form a succinimidyl monomethylpolyethylene glycol glutarate. The succinimidyl ester (mPEG*, denoting the activated PEG intermediate) is then capable of reacting with free amino groups present on collagen (lysine residues) to form a collagen-PEG conjugate wherein one end of the PEG molecule is free or nonbound. Other polymers may be substituted for the monomethyl PEG, as described above. Similarly, the coupling reaction may be carried out using any known method for derivatizing proteins and synthetic polymers. The number of available lysines conjugated may vary from a single residue to 100% of the lysines, preferably 10-50%, and more preferably 20-30%. The number of reactive lysine residues may be determined by standard methods, for example by reaction with TNBS.

A number of sealants may be formed. In situ hydrogel forming compositions are known in the art and can be administered as liquids from a variety of different devices. One such composition provides a photoactivatable mixture of water-soluble co-polyester prepolymers and polyethylene glycol. Another such composition employs block copolymers of Pluronic and Poloxamer that are soluble in cold water, but form insoluble hydrogels that adhere to tissues at body temperature (Leach, et al., Am. J. Obstet. Gynecol. 162:1317-1319 (1990)). Polymerizable cyanoacrylates have also been described for use as tissue adhesives (Ellis, et al., J. Otolaryngol. 19:68-72 (1990)). WO 97/22371 describes two-part synthetic polymer compositions that, when mixed together, form covalent bonds with one another, as well as with exposed tissue surfaces. Similarly, U.S. Pat. No. 5,583,114 describes a two-part composition that is a mixture of protein and a bifunctional crosslinking agent has been described for use as a tissue adhesive.

The device may also be used to prepare and dispense a coagulum-based wound sealant, e.g. a fibrin glue. Such wound sealants may be prepared by mixing a procoagulant-containing solution (which contains fibrinogen) with a solution comprising a fibrinogen activator. Suitable fibrinogen-containing solutions are typically obtained from plasma separated from anticoagulated whole blood by density difference fractionation (e.g., by gravity or centrifugation). Fibrinogen activators are well known and include thrombin and batroxobin, both of which are commercially available. In addition, a variety of additional components can be added to the fibrinogen or fibrinogen activator solutions to modify the characteristics of the coagulum. For example, antifibrinolytics can be employed to regulate the time required for the body to break down the coagulum. Platelets can be included in the fibrinogen solution to increase coagulum strength and adhesion, augment hemostasis, and improve healing. Additionally, calcium can be added to the fibrinogen activator solution to accelerate fibrin crosslinking and stability. Ground bone, demineralized bone matrix, hydroxyapatite, or the like can be included in the fibrinogen activator solution to promote bone regrowth.

Thus, optional additives can be incorporated into the multicomponent composition. For example, an elasticizer such as glycerol may be added to composition to deformability of composition. Similarly, pharmacologically active agents, e.g., organic molecules which exert biological effects in vivo, may be included the composition. Examples of active agents include, without limitation, enzymes, receptor antagonists or agonists, hormones, growth factors, antibiotics, antimicrobial agents, and antibodies.

Various embodiments will be apparent to one of ordinary skill in the art. For example, while particular attention has been given multicomponent compositions that contain PEG-collagen conjugates, other conjugates, such as PEG-PEG and collagen-collagen, may be employed as well. Similarly, while outlet 2 has been described as having a slotted shape, other outlet orifice shapes may be advantageously used as well. Exemplary shapes include, circles, ovals, triangles, rectangles, squares, diamonds, pentagons, etc.

It is to be understood that, while specific exemplary embodiments have been described, modifications will be apparent to those skilled in the art.

All patents, patent applications, and publications mentioned herein are hereby incorporated by reference in their entireties.

I claim:

1. A device, for dispensing a multicomponent composition comprised of a mixture of a plurality of different fluid components, the device comprising:
   a first fluid component inlet adapted to communicate with a source of a first fluid component;
   at least a second fluid component inlet adapted to communicate with a source of at least a second fluid component;
   a tube member;
   a mixing area located downstream from the first and at least second fluid component inlets; and
   an outlet extending from the mixing area,
   wherein the mixing area is adapted to receive a flow of the first fluid component from the first fluid component inlet and a flow of the second fluid component from the second fluid component inlet,
   wherein the mixing area is adapted to disrupt the flow of the first fluid component to mix with the flow of the second fluid component to form a flow of a multicomponent composition within the mixing area,
   wherein the mixing area is adapted to disrupt the flow of the multicomponent composition before the flow of the multicomponent composition exits through the outlet,
   wherein the first and second fluid component inlets are formed as first and second lumens, respectively, within the tube member,
   wherein the mixing area connects to one end of the tubing member, and
   wherein the mixing area includes:
      an open first side that accepts the end of the tube member, wherein the first and second lumens terminate at the open first side;
      a first surface opposite the end of the first lumen that is adapted to disrupt the flow of the first fluid component that enters the mixing area through the end of the first lumen;
      a second side opposite the open first side, wherein the outlet is formed on the second side off-axis from the first and second lumens; and
      a channel having:
         a first segment that directs the flow of the first fluid component to converge with the flow of the second fluid component entering the mixing area through the end of the second lumen to form the flow of the multicomponent composition; and
         a second segment that directs the flow of the multicomponent composition to the outlet,
   wherein the flow of the first fluid component enters into the mixing area in a first direction and is directed by the first surface to a second direction different from the first direction, wherein the first segment directs the flow of the first fluid component in the second direction to converge with the flow of the second fluid component to form the multicomponent composition, wherein the multicomponent composition is directed by the second segment in a third direction that is different from the second direction, and wherein the multicomponent composition is directed by the outlet in a fourth direction that is different from the third.

2. The device of claim 1, wherein the mixing area includes a cavity having a protrusion that extends into the cavity to define the first and second segments within the mixing area.

3. The device of claim 1 further comprising a second surface opposite the end of the second lumen that is adapted to disrupt the flow of the second fluid component that enters the mixing area through the end of the second lumen.

4. The device of claim 1 wherein the first direction differs from the second direction by 90 degrees.

5. The device of claim 1 wherein the second direction differs from the third direction by 180 degrees.

6. The device of claim 1 wherein the third direction differs from the fourth direction by 90 degrees.

7. A nozzle for dispensing a multicomponent composition comprised of a mixture of a plurality of different fluid components, the nozzle comprising:
   a mixing area; and
   an outlet extending from the mixing area,
wherein the mixing area is adapted to receive a flow of a first fluid component and a flow of at least a second fluid component,
wherein the mixing area is adapted to disrupt the flow of the first fluid component to mix with the flow of the at least second fluid component to form a flow of the multicomponent composition within the mixing area,
wherein the mixing area is adapted to disrupt the flow of the multicomponent composition before the flow of the multicomponent composition exits through the outlet,
wherein the mixing area includes:
   an open first side;
   a first surface adapted to disrupt the flow of the first fluid component that enters the mixing area;
   a second side opposite the open first side, wherein the outlet is formed on the second side; and
   a channel having:
      a first segment that directs the flow of the first fluid component to converge with the flow of the second fluid component entering the mixing area to form the flow of the multicomponent composition; and
      a second segment that directs the flow of the multicomponent composition to the outlet, and
wherein the mixing area includes a cavity having a protrusion that extends into the cavity to define the first and second segments within the mixing area, wherein the first and second segments extend in opposite directions within the mixing area.

8. The nozzle of claim 7, wherein the first segment extends in a direction 90 degrees from the direction in which the flow of the first fluid component enters the mixing area, and wherein the second segment extends in a direction 180 degrees from the direction in which the first segment extends.

9. The nozzle of claim 8, wherein the outlet extends in a direction 90 degrees from the direction in which the second segment extends.

10. A nozzle for dispensing a multicomponent composition comprised of a mixture of a plurality of different fluid components, the nozzle comprising:
   a mixing area;
   an outlet extending from the mixing area; and
   a notch that fits into a groove running along at least a portion of the length of a tube member to orient the nozzle to the tube member;
wherein the mixing area is adapted to receive a flow of a first fluid component and a flow of at least a second fluid component,
wherein the mixing area is adapted to disrupt the flow of the first fluid component to mix with the flow of the at least second fluid component to form a flow of the multicomponent composition within the mixing area,
wherein the mixing area is adapted to disrupt the flow of the multicomponent composition before the flow of the multicomponent composition exits through the outlet,
wherein the tube member includes a first and second fluid component inlets formed as first and second lumens, respectively, within the tube member, and wherein the first and second fluid components are delivered to the mixing area through the first and second lumens, and
wherein the tube member has third and fourth fluid component inlets formed as third and fourth lumens, respectively, within the tube member, and wherein a carrier fluid is delivered to the mixing area through the third and fourth lumens.

11. The nozzle of claim 10, the wherein the outlet is formed off-axis from the first and second lumens.

12. A method for dispensing a multicomponent composition using a nozzle, the method comprising:
   a) receiving a flow of a first fluid component into a mixing area in the nozzle;
   b) receiving a flow of at least a second fluid component into the mixing area;
   c) disrupting the flow of the first fluid component to mix with the flow of the at least second fluid component to form a flow of a multicomponent composition within the mixing area;
   d) disrupting the flow of the multicomponent composition within the mixing area; and
   e) after d), dispensing the multicomponent composition from the mixing area through an outlet,
wherein the flow of the first fluid component in b) enters into the mixing area in a first direction,
wherein c) comprises directing the flow of the first fluid component in a second direction different from the first direction,
wherein d) comprises directing the flow of the multicomponent composition in a third direction that is different from the second direction, and
wherein e) comprises directing the multicomponent composition in a fourth direction that is different from the third direction.

13. The method of claim 12 wherein the first direction differs from the second direction by 90 degrees, the second direction differs from the third direction by 180 degrees, and the third direction differs from the fourth direction by 90 degrees.

14. A method for forming a device for dispensing a multicomponent composition comprised of a mixture of a plurality of different fluid components, the method comprising:
   forming a mixing area; and
   forming an outlet extending from the mixing area,
wherein the mixing area is adapted to receive a flow of a first fluid component and a flow of at least a second fluid component,
wherein the mixing area is adapted to disrupt the flow of the first fluid component to mix with the flow of the at least second fluid component to form a flow of the multicomponent composition within the mixing area,
wherein the mixing area is adapted to disrupt the flow of the multicomponent composition before the flow of the multicomponent composition exits through the outlet, and
wherein the mixing area is formed with:
   an open first side;
   a first surface adapted to disrupt the flow of the first fluid component that enters the mixing area;
   a second side opposite the open first side, wherein the outlet is formed on the second side;
   a channel having:
      a first segment that directs the flow of the first fluid component to converge with the flow of the second fluid component entering the mixing area to form the flow of the multicomponent composition; and
      a second segment that directs the flow of the multicomponent composition to the outlet, and
wherein the mixing area is formed with a cavity having a protrusion that extends into the cavity to define the first and second segments within the mixing area, and wherein the first and second segments are formed to extend in opposite directions within the mixing area.

15. The method of claim 14, wherein the first segment is formed to extend in a direction 90 degrees from the direction in which the flow of the first fluid component enters the mixing area, and wherein the second segment is formed to extend in a direction 180 degrees from the direction in which the first segment extends.

16. The method of claim 15, wherein the outlet is formed to extend in a direction 90 degrees from the direction in which the second segment extends.

17. A method for forming a device for dispensing a multi-component composition comprised of a mixture of a plurality of different fluid components, the method comprising:
forming a mixing area, and
forming an outlet extending from the mixing area; and
forming a tube member having first and second fluid component inlets formed as first and second lumens, respectively, within the tube member,
wherein the mixing area is adapted to receive a flow of a first fluid component and a flow of at least a second fluid component,
wherein the mixing area is adapted to disrupt the flow of the first fluid component to mix with the flow of the at least second fluid component to form a flow of multicomponent composition within the mixing area,
wherein the mixing area is adapted to disrupt the flow of the multicomponent composition before the flow of multicomponent composition exits through the outlet,
wherein the mixing area is formed within a nozzle,
wherein the tube member has third and fourth fluid component inlets formed as third and fourth lumens, respectively, within the tube member, and
wherein a carrier fluid is delivered to the mixing area through the third and fourth lumens.

18. The method of claim 17, wherein the nozzle is formed with a notch that fits into a groove formed along at least a portion of the length of the tube member to orient the nozzle to the tube member such that the third lumen is in-line with the outlet.

19. A device for dispensing a multicomponent composition comprised of a mixture of a plurality of different fluid components, the device comprising:
a first fluid component inlet adapted to communicate with a source of a first fluid component;
at least a second fluid component inlet adapted to communicate with a source of at least a second fluid component;
a tube member;
a mixing area located downstream from the first and at least second fluid component inlets; and
an outlet extending from the mixing area,
wherein the mixing area is adapted to receive a flow of the first fluid component from the first fluid component inlet and a flow of the second fluid component from the second fluid component inlet,
wherein the mixing area is adapted to disrupt the flow of the first fluid component to mix with the flow of the second fluid component to form a flow of a multicomponent composition within the mixing area,
wherein the mixing area is adapted to disrupt the flow of the multicomponent composition before the flow of the multicomponent composition exits through the outlet,
wherein the first and second fluid component inlets are formed as first and second lumens, respectively, within the tube member,
wherein the mixing area connects to one end of the tubing member, and
wherein the mixing area includes:
an open first side that accepts the end of the tube member, wherein the first and second lumens terminate at the open first side;
a first surface opposite the end of the first lumen that is adapted to disrupt the flow of the first fluid component that enters the mixing area through the end of the first lumen;
a second side opposite the open first side, wherein the outlet is formed on the second side off axis from the first and second lumens; and
a channel having:
a first segment that directs the flow of the first fluid component to converge with the flow of the second fluid component entering the mixing area through the end of the second lumen to form the flow of the multicomponent composition; and
a second segment that directs the flow of the multicomponent composition to the outlet,
wherein the first and second segments extend in opposite directions within the mixing area.

* * * * *